(12) United States Patent
George et al.

(10) Patent No.: US 7,946,975 B2
(45) Date of Patent: May 24, 2011

(54) FLUID RESERVOIR FOR PENILE IMPLANT DEVICES

(75) Inventors: Stephanie A. George, St. Louis Park, MN (US); Jon D. Albrecht, Hutchinson, MN (US); Robert L. Rykhus, Edina, MN (US); Steven K. Wilson, LaQuinta, CA (US)

(73) Assignee: AMS Research Corporation, Minnetonka, MN (US)

( * ) Notice: Subject to any disclaimer, the term of this patent is extended or adjusted under 35 U.S.C. 154(b) by 1416 days.

(21) Appl. No.: 11/279,035

(22) Filed: Apr. 7, 2006

(65) Prior Publication Data
US 2006/0235267 A1    Oct. 19, 2006

Related U.S. Application Data

(60) Provisional application No. 60/669,427, filed on Apr. 8, 2005, provisional application No. 60/669,673, filed on Apr. 8, 2005.

(51) Int. Cl.
*A61F 2/02* (2006.01)
(52) U.S. Cl. ......................................................... 600/30
(58) Field of Classification Search ............... 600/38–41; 128/897, 898
See application file for complete search history.

(56) References Cited

U.S. PATENT DOCUMENTS

| | | | |
|---|---|---|---|
| 988,120 A | 3/1911 | Lott | |
| 1,863,057 A | 6/1932 | Innes | |
| 2,586,575 A | 2/1952 | Arthur | |
| 2,786,718 A | 3/1957 | Middlestadt | |
| 3,228,731 A | 1/1966 | Valentine | |
| 3,312,215 A | 4/1967 | Silber | |
| 3,344,791 A | 10/1967 | Foderick | |
| 3,397,699 A | 8/1968 | Kohl | |
| 3,503,400 A | 3/1970 | Osthagen et al. | |
| 3,510,029 A | 5/1970 | Doyle | |
| 3,642,004 A | 2/1972 | Osthagen et al. | |
| 3,731,670 A | 5/1973 | Loe | |

(Continued)

FOREIGN PATENT DOCUMENTS

DE     2537506 A1    8/1975

(Continued)

OTHER PUBLICATIONS

Abouassaly, R. et al, "Antibiotic-coated medical devices: with an emphasis on inflatable penile prosthesis", Asian J Androl. Sep. 2004; 6: 249-57.

(Continued)

*Primary Examiner* — Samuel G Gilbert
(74) *Attorney, Agent, or Firm* — Kimberly K. Baxter; Gregory L. Koeller

(57) ABSTRACT

The invention is directed to a medical device, particularly a penile prosthesis, that includes an implantable element and a reservoir. The implantable element is configured to be implanted within the pelvic region of a patient and is designed to be capable of inflation and deflation via fluid transfer to and from the element. The reservoir is coupled to the implantable element. The fluid is drawn from the reservoir for inflation of the implantable element and returned to the reservoir for the deflation. The reservoir is approximately one inch or less in depth. The minimal depth enables the fluid reservoir to be placed in front of the puborectalis muscle and behind the abdominal fascia without being seen on an external view of the patient.

25 Claims, 7 Drawing Sheets

U.S. PATENT DOCUMENTS

| | | |
|---|---|---|
| 3,797,478 A | 3/1974 | Walsh et al. |
| 3,812,841 A | 5/1974 | Isaacson |
| 3,853,122 A | 12/1974 | Strauch et al. |
| 3,954,102 A * | 5/1976 | Buuck .............................. 600/40 |
| 4,009,711 A | 3/1977 | Uson |
| 4,201,202 A | 5/1980 | Finney et al. |
| 4,204,530 A | 5/1980 | Finney |
| 4,222,377 A | 9/1980 | Burton |
| 4,224,934 A | 9/1980 | Scott et al. |
| 4,235,227 A | 11/1980 | Yamanaka |
| 4,256,093 A | 3/1981 | Helms et al. |
| 4,267,829 A | 5/1981 | Burton et al. |
| 4,318,396 A | 3/1982 | Finney |
| 4,342,308 A | 8/1982 | Trick |
| 4,344,434 A | 8/1982 | Robertson |
| 4,353,360 A | 10/1982 | Finney et al. |
| 4,360,010 A | 11/1982 | Finney |
| 4,364,379 A | 12/1982 | Finney |
| 4,369,771 A | 1/1983 | Trick |
| 4,378,792 A | 4/1983 | Finney |
| 4,383,525 A | 5/1983 | Scott et al. |
| 4,399,811 A | 8/1983 | Finney et al. |
| 4,399,812 A | 8/1983 | Whitehead |
| 4,404,968 A | 9/1983 | Evans, Sr. |
| 4,407,278 A | 10/1983 | Burton et al. |
| 4,412,530 A | 11/1983 | Burton |
| 4,424,807 A | 1/1984 | Evans, Sr. |
| 4,437,457 A | 3/1984 | Trick et al. |
| 4,441,491 A | 4/1984 | Evans, Sr. |
| 4,449,520 A | 5/1984 | Palomar et al. |
| 4,453,536 A | 6/1984 | Abild |
| 4,457,335 A | 7/1984 | Trick |
| 4,489,732 A | 12/1984 | Hasson |
| 4,523,584 A | 6/1985 | Yachia et al. |
| 4,532,920 A | 8/1985 | Finney |
| 4,537,183 A | 8/1985 | Fogarty |
| 4,550,719 A | 11/1985 | Finney et al. |
| 4,550,720 A | 11/1985 | Trick |
| 4,553,959 A | 11/1985 | Hickey et al. |
| 4,558,693 A | 12/1985 | Lash et al. |
| 4,559,931 A | 12/1985 | Fischell |
| 4,566,446 A | 1/1986 | Fogarty |
| 4,571,241 A | 2/1986 | Christopher |
| 4,572,168 A | 2/1986 | Fischell |
| 4,574,792 A | 3/1986 | Trick |
| 4,587,954 A | 5/1986 | Haber |
| 4,590,927 A | 5/1986 | Porter et al. |
| 4,596,242 A * | 6/1986 | Fischell .......................... 600/40 |
| 4,602,625 A | 7/1986 | Yachia et al. |
| 4,604,994 A | 8/1986 | Sealfon |
| 4,611,584 A | 9/1986 | Finney |
| 4,622,958 A | 11/1986 | Finney |
| 4,632,435 A | 12/1986 | Polyak |
| 4,651,721 A | 3/1987 | Mikulich et al. |
| 4,653,485 A | 3/1987 | Fishell |
| 4,664,100 A | 5/1987 | Rudloff |
| 4,665,903 A | 5/1987 | Whitehead |
| 4,671,261 A * | 6/1987 | Fischell .......................... 600/40 |
| 4,682,583 A | 7/1987 | Burton et al. |
| 4,682,589 A | 7/1987 | Finney |
| 4,710,169 A | 12/1987 | Christopher |
| 4,718,410 A | 1/1988 | Hakky |
| 4,724,830 A | 2/1988 | Fischell |
| 4,726,360 A | 2/1988 | Trick et al. |
| 4,730,607 A | 3/1988 | Fischell |
| 4,766,889 A | 8/1988 | Trick et al. |
| 4,773,403 A | 9/1988 | Daly |
| 4,782,826 A | 11/1988 | Fogarty |
| 4,790,298 A | 12/1988 | Trick |
| 4,791,917 A | 12/1988 | Finney |
| 4,807,608 A | 2/1989 | Levius |
| 4,829,990 A | 5/1989 | Thuroff et al. |
| 4,829,991 A | 5/1989 | Boeck |
| 4,850,963 A | 7/1989 | Sparks et al. |
| 4,881,530 A * | 11/1989 | Trick .............................. 600/40 |
| 4,895,139 A | 1/1990 | Hauschild et al. |
| 4,917,110 A | 4/1990 | Trick |
| 4,932,938 A | 6/1990 | Goldberg et al. |
| 4,944,732 A | 7/1990 | Russo |
| 4,958,630 A | 9/1990 | Rosenbluth et al. |
| 4,968,294 A | 11/1990 | Salama |
| 4,988,357 A | 1/1991 | Koss |
| 5,010,882 A | 4/1991 | Polyak et al. |
| 5,030,199 A | 7/1991 | Barwick et al. |
| 5,034,009 A | 7/1991 | Mouchel |
| 5,041,092 A | 8/1991 | Barwick |
| 5,048,510 A | 9/1991 | Hauschild et al. |
| 5,048,511 A | 9/1991 | Rosenbluth et al. |
| 5,052,383 A | 10/1991 | Chabert |
| 5,062,416 A | 11/1991 | Stucks |
| 5,062,417 A | 11/1991 | Cowen |
| 5,063,914 A | 11/1991 | Cowen |
| 5,067,485 A | 11/1991 | Cowen |
| 5,074,849 A | 12/1991 | Sachse |
| 5,085,650 A | 2/1992 | Giglio |
| 5,088,980 A | 2/1992 | Leighton |
| 5,090,424 A | 2/1992 | Simon et al. |
| 5,101,813 A | 4/1992 | Trick |
| 5,112,295 A | 5/1992 | Zinner et al. |
| 5,114,398 A | 5/1992 | Trick et al. |
| 5,129,880 A | 7/1992 | Grundei |
| 5,131,906 A | 7/1992 | Chen |
| 5,141,509 A | 8/1992 | Burton et al. |
| 5,158,111 A | 10/1992 | Lambert et al. |
| 5,167,611 A | 12/1992 | Cowan |
| 5,171,272 A | 12/1992 | Levius |
| 5,186,180 A | 2/1993 | Bellas |
| 5,250,020 A | 10/1993 | Bley |
| 5,263,981 A | 11/1993 | Polyak et al. |
| 5,328,293 A | 7/1994 | Keefe |
| 5,344,388 A | 9/1994 | Maxwell et al. |
| 5,433,694 A | 7/1995 | Lim |
| 5,518,499 A | 5/1996 | Agar |
| 5,595,331 A | 1/1997 | Leistner |
| 5,678,768 A | 10/1997 | Gager et al. |
| 5,704,895 A | 1/1998 | Scott et al. |
| 5,851,176 A | 12/1998 | Willard |
| 5,893,826 A | 4/1999 | Salama |
| 5,895,424 A | 4/1999 | Steele, Sr. et al. |
| 6,171,233 B1 | 1/2001 | Willard |
| 6,443,887 B1 | 9/2002 | Derus et al. |
| 6,533,719 B2 | 3/2003 | Kuyava et al. |
| 6,558,315 B1 | 5/2003 | Kuyava |
| 6,723,042 B2 | 4/2004 | Almli et al. |
| 6,730,017 B2 | 5/2004 | Waldack et al. |
| 6,733,527 B2 | 5/2004 | Koyfman |
| 6,929,599 B2 | 8/2005 | Westrum, Jr. |
| 6,935,847 B2 | 8/2005 | Kuyava et al. |
| 6,991,601 B2 | 1/2006 | Kuyava et al. |
| 7,066,877 B2 | 6/2006 | Kuyava |
| 7,066,878 B2 | 6/2006 | Eid |
| 7,169,103 B2 | 1/2007 | Ling et al. |
| 7,244,227 B2 | 7/2007 | Morningstar |
| 7,250,026 B2 | 7/2007 | Kuyava |
| 7,350,538 B2 | 4/2008 | Kuyava et al. |
| 7,390,296 B2 | 6/2008 | Mische |
| 7,438,682 B2 | 10/2008 | Henkel et al. |
| 7,491,164 B2 | 2/2009 | Choi et al. |
| 7,637,861 B2 | 12/2009 | Kuyava et al. |
| 2002/0033564 A1 | 3/2002 | Koyfman |
| 2002/0082473 A1 | 6/2002 | Henkel et al. |
| 2002/0082709 A1 | 6/2002 | Almli et al. |
| 2002/0091302 A1 | 7/2002 | Kuyava et al. |
| 2003/0028076 A1 | 2/2003 | Kuyava et al. |
| 2004/0193005 A1 | 9/2004 | Almli |
| 2004/0220447 A1 | 11/2004 | Morningstar |
| 2004/0220448 A1 | 11/2004 | Henkel |
| 2005/0250982 A1 | 11/2005 | Kuyava et al. |
| 2006/0135845 A1 | 6/2006 | Kuyava et al. |

FOREIGN PATENT DOCUMENTS

| | | |
|---|---|---|
| EP | 0051420 | 5/1982 |
| EP | 0065853 | 12/1982 |
| EP | 0682923 | 11/1995 |
| EP | 0925764 | 6/1999 |
| GB | 2160777 | 1/1986 |
| GB | 2192546 | 1/1988 |

| | | |
|---|---|---|
| WO | WO8000302 | 3/1980 |
| WO | WO8500513 | 2/1985 |
| WO | WO9203107 | 3/1992 |
| WO | WO9404095 | 3/1994 |
| WO | WO2051339 | 7/2002 |

OTHER PUBLICATIONS

Agrawal, V. et al. "An audit of implanted penile prostheses in the UK", BJU International 98, 293-295 (2006).
Akin-Olugbade, O. et al, "Determinants of Patient Satisfaction Following Penile Prosthesis Surgery", J Sex Med 2006; 3: 743-48.
Al-Najar, A. et al, "Should being aged over 70 years hinder penile prosthesis implantation?", BJU International 2009 1-4.
AMS 700 CX Penile Prosthesis (Brochure)2 pages 1999.
AMS 700 Inflatable Penile Prosthesis Product Line 45 pages (1992).
AMS (Brochure) 700 Series Tactile (Pump 2 pages) 2004.
AMS (Brochure) Ultrex/Ultrex Plus (10 Pages)(1998).
AMS Ambicor Penile Prosthesis (Brochure) 1996.
Merino, G. Atienza, "Penile Prosthesis for the treatment of erectile dysfunction" Actas Urol Esp. 2006; 30(2): 159-69.
Candela, J. et al "Three-piece inflatable penile prosthesis implantation: . . . " J La State Med Soc 148:296-301 (1996).
Daitch, J. et al, "Long-Term Mechanical Reliability of AMS 700 Series Inflatable Penile Prostheses: Comparison . . . " J. Urol. 158: 1400-1402; Oct. 1997.
Delk, J. "Early Experience with the American Medical Systems New Tactile Pump: Results of a Multicenter Study" J Sex med 2005; 2: 266-271.
Deuk Choi, Y. et al. "Mechanical Reliability of the AMS 700CXM Inflatable Penile Prosthesis for the Treatment of Male Erectile Dysfunction" J. Urol 168, 822-824, Mar. 2001.
Deveci, S. et al "Penile Length Alterations following Penile Prosthesis Surgery" European Urol. 51 (2007) 1128-31.
Gefen, A. "Stresses in the normal and diabetic human penis following implantation of an inflatable prosthesis." Med. Biol. Eng. Comput., 1999, 37, 625-31.
Garber, B. "Inflatable penile prostheses for the treatment of erectile dysfunction." Exper Rev. Med. Devices 2(3), 341-50 (2005).
Gefen, A et al. "A biomechanical model of Peyronie's disease" J. Biomech.33 (2000) 1739-44.
Gefen, A et al. "Optimization of Design and Surgical Positioning of Inflatable Penile Prostheses" Annals of Biomed. Eng. 28 (2000) 619-28.
Henry, G "Advances in Penile Prosthesis Design", Current Sexual Health Reports 2007, 4:15-19.
InhibiZone Antibiotic Surface Treatment, (AMS Brochure) 4pgs 2001.
Kadioglu, A. et al. "Surgical Treatment of Peyronie's Disease: A Critical Analysis" European urology 50 ( 2 0 0 6 ) 235-248.
Kava, B et al "Efficacy and Patient Satisfaction Associated with Penile Prosthesis Revision Surgery" J Sex Med 2007;4:509-518.
Lazarou, S., et al, "Technical Advances in Penile Prostheses" J Long-Term Effects of Med. Imp. 16(3):235-247 (2006).
Levine, L et al, "Mechanical Reliability and Safety of, and Patient Satisfaction With the Ambicor Inflatable Penile Prosthesis: Results of a 2 Center Study" J Urol vol. 166, 932-937, Sep. 2001.
Lumen, N. "Phalloplasty: A Valuable Treatment for Males with Penile Insufficiency", Urology 71 (2), 2008 272-276.
Lux, M. et al. "Outcomes and Satisfaction Rates for the Redesigned 2-Piece Penile Prosthesis" J Urol. vol. 177, 262-266, Jan. 2007.
Mentor New from Mentor Urology Alpha I Narrow-Base (Brochure) 2pgs 1996.
Mentor Alpha I Inflatable Penile Prosthesis (Brochure) 2 pgs Jul. 1996.
Mentor Surgical Protocol Alpha I Inflatable Penile Prosthesis 17pgs May 1998.
Mentor Patient Guide for Alpha I Inflatable Penile Implant (Brochure) 2pgs 1997.
Montague, D., "Penile Prosthesis Implantation for End-Stage Erectile Dysfunction After Radical Prostatectomy" Reviews in Urol. vol. 7 Suppl. 2 2005 S51-S57.
Mulcahy, J. "Distal Corporoplasty for Lateral Extrusion of Penile Prosthesis Cylinders" J. Urol. vol. 161, 193-195 Jan. 1999.
Murphy, AM., et al. "Failure of the Ambicors inflatable penile prosthesis to deflate" International Journal of Impotence Research (2005) 17, 291-292.
"Parylene Micro Coating" AMS Brochure, 4 pgs. 2000.
Sadeghi-Nejad, H. "Penile Prosthesis Surgery: A Review of Prosthetic Devices and Associated Complications" J Sex Med 2007;4:296-309.
Scarzella, IG,. et al. "Use of Ambicor Penile Prosthesis in Peyronie's Disease and as Replacement for Malfunctioning AMS 700 Devices", J Sex Med 2004; Suppl. 1.
Ultrex Plus Penile Prosthesis (AMS Advertisement) 1 pg (1992).
Wang, Shyh-Jen, et al "Hardness evaluation of penile prostheses" International Journal of Urology (2006) 13, 569-572.
Mentor Surgical Protocol Alpha I Inflatable Penile Prosthesis 15pgs 1998.
Mentor Urology Products, (Brochure), Mentor, 20 pages (1998).
Hellstrom, WJG, "Three-piece inflatable penile prosthesis components (surgical pearls on reservoirs, pumps, and rear-tip extenders)" International Journal of Impotence Research (2003) 15, Suppl 5, S136-S138.
Kim, Sae-Chui, "Mechanical Reliability of AMS Hydraulic Penile Prostheses" J. of Korean Med. Sci. 10(6); 422-425, Dec. 1995.
Mooreville, M. et al "Implantation of Inflatable Penile Prosthesis in Patients With Severe Corporeal Fibrosis: Introduction of a New Penile Cavernotome" J. Urol 162, 2054-2057, Dec. 1999.
Montague, DK., "Early Experience with the Controlled Girth and Length Expanding Cylinder of the American Medical Systems Ultrex Penile Prosthesis", J. Urol. 148; 1444-1446, Nov. 1992.
Montague, DK "Cylinder Sizing: less is more" International Journal of Impotence Research (2003) 15, Suppl 5, S132-S133.
Montague, DK et al. "AMS 3-Piece Inflatable Penile Prosthesis Implantation in Men with Peyronie's Disease: Comparison of Cx and Ultrex Cylinders" J. Urol. 156, 1633-1635, Nov. 1996.
Montague, DK et al, "Penile Prosthesis Infections" International Journal of Impotence Research (2001) 13, 326-328.
Malloy, T., et al., "Improved Mechanical Survival with Revised Model Inflatable Penile Prosthesis Using Rear-Tip Extenders", J Urol. 128 Sep. 1982 489-491.
Chang, Yao-Jen, et al "Penile Prosthesis Implantation" eMedicine http://www.emedicine.com/med/topic3047.htm 19 pages (2003).
Gregory, J., et al., "The Inflatable Penile Prosthesis: Failure of the Rear Tip Extender in Reducing the Incidence of Cylinder Leakage" J Urol. vol. 131 668-669 (1984).
Joseph, D., et al., "Bilateral Dislocating of Rear Tip Extenders from the Inflatable Penile Prosthesis" J Urol vol. 128, Dec. 1982 1317-1318.

* cited by examiner

FLUID RESERVOIR FOR PENILE IMPLANT DEVICES

CLAIM TO PRIORITY

The present application claims priority to U.S. provisional patent application 60/669,427, filed Apr. 8, 2005 and entitled "Fluid Reservoirs for Penile Implant Devices" and to U.S. provisional patent application 60/669,673, filed Apr. 8, 2005 and entitled "Fluid Reservoirs for Penile Implant Devices". The noted provisional patent applications are hereby incorporated by reference.

FIELD OF THE INVENTION

The present invention relates generally to surgical implant devices for containing fluid. More particularly, the present invention relates to fluid reservoirs for use with penile implant devices and related methods for implantation of such reservoirs.

BACKGROUND OF THE INVENTION

One common treatment for erectile dysfunction includes the use of a penile implant device. A particular type of penile implant device, commonly known as a three-piece device, includes a pair of inflatable cylindrical prostheses that are implanted into the corpus cavernosae of the penis. The cylindrical prostheses are connected to a fluid-filled reservoir through a pump and valve assembly. Such a pump and valve assembly is typically implanted into the scrotum of the patient, while the reservoir is implanted in the abdomen. Tubing is used to connect each penile prosthesis to the pump, and additional tubing is used to connect the pump to the reservoir. To activate the penile implant device, the patient can typically actuate the pump using one of a variety of methods that cause fluid to be transferred from the reservoir through the pump and into the prostheses. This results in the inflation of the prostheses and produces rigidity for a normal erection. Then, when the patient desires to deflate the prostheses, a valve assembly within the pump in such a manner that the fluid in the prostheses is released back into the reservoir. Additional manipulation of the cylindrical prostheses may also be required. This removal of fluid from the cylindrical prostheses returns the penis to a flaccid state while simultaneously refilling the reservoir with fluid.

The reservoir used in these three-piece systems is usually in the form of a flexible bag or bladder that can expand and contract in volume with movement of fluid to and from the reservoir. In many cases, the reservoir is relatively spherical in shape, which requires placement of the reservoir in a location in the patient's body where there is sufficient space to allow the system to operate properly and to keep the reservoir from causing a visible protrusion outside the patient's body. Thus, spherical reservoirs are often placed below the puborectalis muscle during surgical implantation of the penile implant device, which requires a "blind" approach. This approach can be relatively difficult, particularly for less experienced surgeons. Thus, it is desirable to provide a reservoir that can offer an easier surgical approach for the doctor, such as a surgical procedure that eliminates the requirement to position the reservoir behind the puborectalis muscle.

SUMMARY OF THE INVENTION

The invention relates to devices and methods that overcome certain shortcomings of the prior fluid reservoirs fro penile implant devices. In particular, the invention provides fluid reservoirs with a design that eliminates the requirement for placement below the puborectalis muscle, anterior to the transversalis fascia. Thus, the invention provides fluid reservoirs having sufficiently small depth that enables them to be implanted submuscularly in the lower abdomen where they will be virtually undetectable from outside the patient's body. In particular, the reservoir length and width are designed and/or chose so that the reservoir can fit in the patient lateral to the midline of the lower abdomen. This location can be relatively easy for the surgeon to reach during implantation of the device, and provides for a less intrusive device implantation than the surgery required for some other reservoirs.

BRIEF DESCRIPTION OF THE DRAWINGS

The invention will be further explained with reference to the appended Figures, wherein like structure is referred to by like numerals through the several views, and wherein.

DETAILED DESCRIPTION

Figure 1:
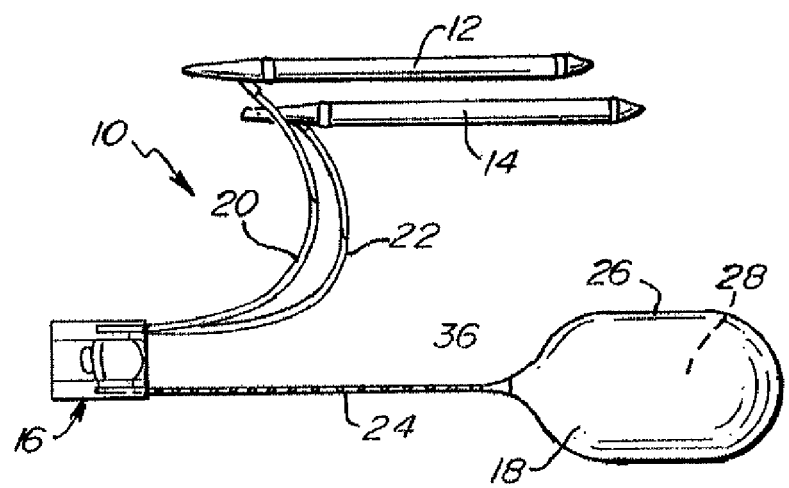
FIG. 1 is a top view of a three piece implantable prosthesis device having a pair of penile prostheses, a pump, and a reservoir of the present invention.
Figure 2:
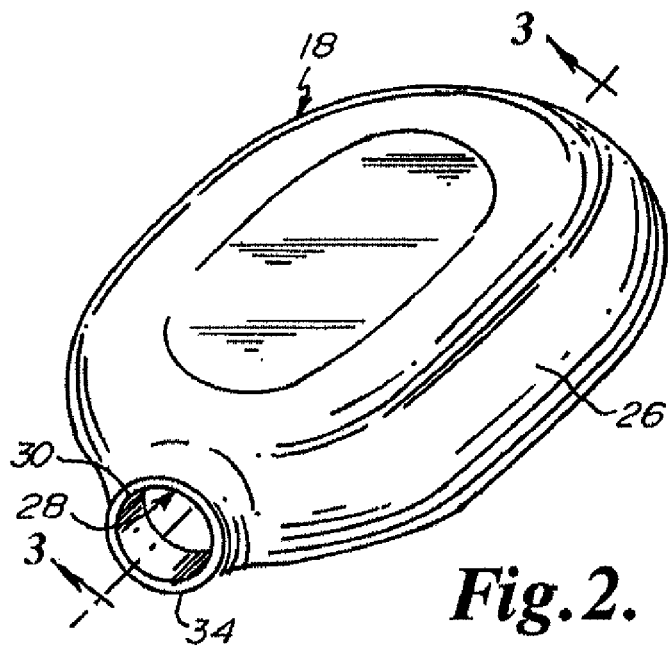
FIG. 2 is a perspective view of the preferred embodiment of the reservoir of the present invention.

Referring now to the Figures, wherein the components are labeled with like numerals throughout the several Figures, and initially to FIG. 1, the preferred configuration of a surgically implantable penile prosthesis device 10 having a three-piece design is illustrated. As shown, device 10 generally includes first and second inflatable penile cylinders 12 and 14, respectively, a pump 16, and a reservoir 18 in accordance with the invention. First penile cylinder 12 is fluidly coupled to pump 16 by a tube 20 and second penile cylinder 14 is fluidly coupled to pump 16 by a tube 22. Pump 126 is fluidly coupled to reservoir 18 by tube 24. When device 10 is implanted into a patient, cylinders 12 and 14 are surgically located in the corpus cavernosa regions of a penis and pump 16 is located within the scrotum of a patient, while reservoir 18 is located within the abdominal area of the patient. In user, the patient can activate pump 16 in some manner (e.g., squeezing the body or other portion of pump 16 in a particular way to open the valve) to move fluid from reservoir 18 to inflate penile cylinders 12 and 14 and provide an erection. Similarly, the patient can activate pump 16 in some manner to return fluid to reservoir 18 and thereby deflate penile cylinders 12 and 14 and return the cylinders to a flaccid condition.

A wide variety of configurations of penile prosthesis devices may utilize a reservoir 18 of the type described here, and any of the alternative reservoirs described herein, wherein device 10 of FIG. 1 is intended to illustrate only representative system in which a reservoir 18 may be used. For example, a number of different types of pump configurations may be used, such as those that require very little manipulation to move fluid between the reservoir and cylinders, or those that instead require the user to repeatedly squeeze the pump body to cause fluid transfer within the penile prosthesis device or system. In addition, devices having greater or fewer components than the number that are used in a three-piece design can utilize the advantages of the reservoirs of the present invention.

FIGS. 2 through 8 further illustrate the preferred embodiment of reservoir 18 of the present invention, which generally includes a shell 26 having an interior space 28 and an opening 30 at one end. A neck portion 34 extends from shell 26 at opening 30 for connection with a tube, such as tube 24 of prosthesis device 10. Neck portion 34 may be directly connected to tube 24 or another component, or an adapter or other device can be used between neck portion 34 and tube 24 to provide a smooth transition between these two components. Any additional devices or adapters that are provided between tube 24 and neck portion 34 may be directly molded to one or both components, or may be adhered or otherwise attached to one or both components to prevent fluid leakage and allow for smooth fluid flow. In any case, the transitions between tube 24 and neck portion 34 should not inhibit the flow of fluid to and from interior space 28 of reservoir 18.

Figure 3:
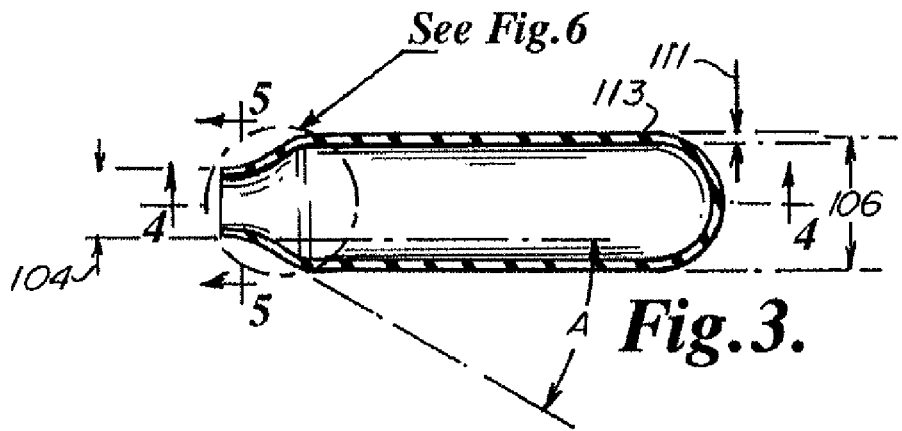
FIG. 3 is a cross-sectional view of the reservoir taken along line 3-3 of FIG. 2.
Figure 4:
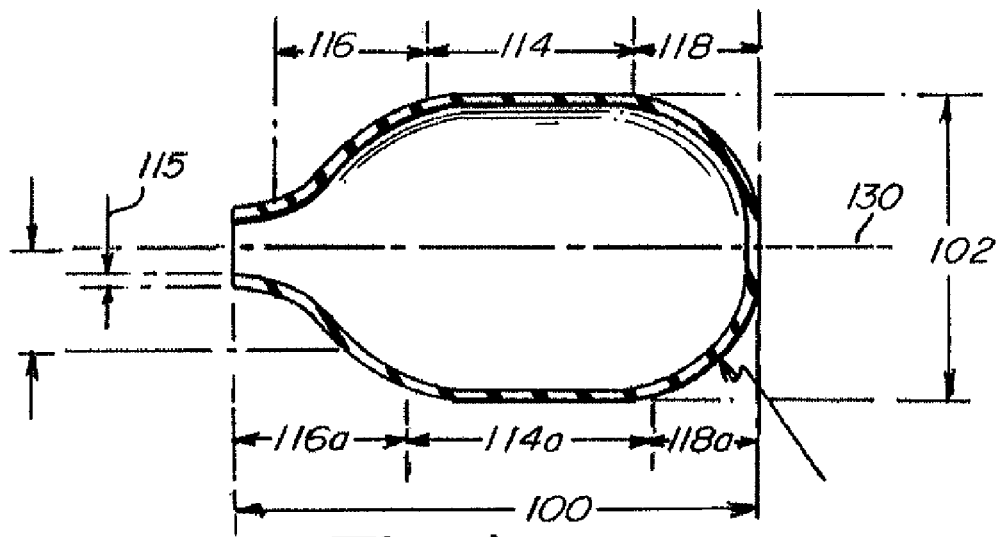
FIG. 4 is a cross-sectional view of the reservoir taken along line 4-4 of FIG. 3.
Figure 5:
FIG. 5 is a cross-sectional view of the reservoir taken along line 5-5 of FIG. 3.
Figure 6:
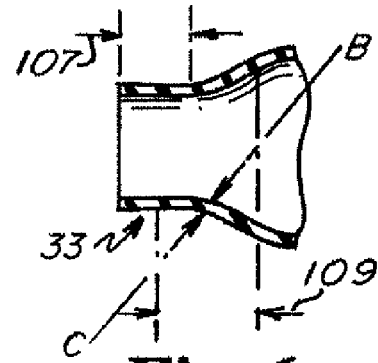
FIG. 6 a an exploded view of the portion of FIG. 3 designated by circle 6.
Figure 7:
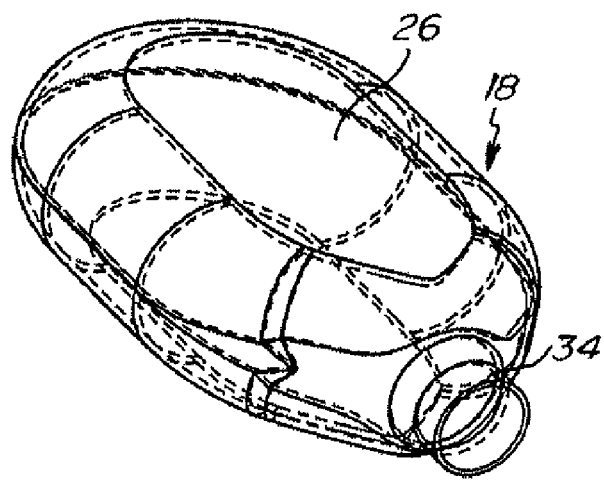
FIG. 7 is a perspective view of the reservoir of FIG. 2 with hidden lines showing the contours of the reservoir.

Referring particularly to FIGS. 3 and 4, reservoir 18 is generally provided in an exemplary flat, elongated shape as illustrated, which includes shell 26 having a length 100, a width 102, and a depth or thickness 106. Reservoir 18 is preferably symmetrical or generally symmetrical about its centerline 130, shown in FIG. 4. Width 102 is preferably relatively constant along at least a portion of length 100 and is more preferably relatively constant along at least half of the length 100 of shell 26, although it is possible that width is constant along less than half of the length 100 of shell 26. A straight portion 114 of one edge of shell 26 is located between curved portions 116 and 118. Curved portion 116, which is shown on the top edge of shell 26 in FIG. 4, has a corresponding mirror image curved portion 116a on the opposite or bottom edge of shell 26. Curved portions 116 and 116a provide the outside boundary for a portion of shell 26 that decreases in width from width 102 at straight portions 114 and 114a down toward a diameter 104 of neck portion 34, see also the section provided in FIG. 5 depicting the diameter 104 of neck portion 34. The angle of transition from the neck portion 34 to the shell portion 26 is approximately angle A. FIG. 6 further details the transition area 33 from neck portion 34 to shell 26. As shown, the transition area 33 is provided with an inner radius B and an outer radius C. Additionally, neck portion 34 is defined by a neck portion length 107 and a transition area length 109

Curved portion 118, which is shown on the top edge of shell 26 in FIG. 4, is a curved edge that extends from straight portion 114 on one edge of shell 26 to the centerline 130 of shell 26. Curved portion 118a continues from curved portion 118 around the bottom edge of shell 26 and around to the straight portion 114a of shell 26. In this preferred embodiment, length 100 has a greater length than width 102, and both length 100 and width 102 are greater in length than thickness or depth 106.

Referring again to FIGS. 3 and 4, the thickness 111 of the wall 113 of the shell 26 can be appreciated. The thickness 111 of the wall 113 smoothly blends to the reduced thickness 115 of the neck portion wall 117, e.g., from a thickness of 0.040 inches in the shell to a thickness of 0.030 inches in the neck portion. In the preferred embodiment, the thickness 111 of the wall 113 is preferably of a substantially consistent thickness, however, the thickness can vary without departing from the spirit or scope of the invention. The contours of the reservoir may be observed in FIG. 7.

Additional features may be added to the reservoir to maintain the integrity of the shell shape. One example is to provide an internal or external support material that is attached to or otherwise situated relative to the shell. The internal or external support may be a wire, such as may be constructed of nitinol, and may be shaped to generally match the outer shape of the reservoir. The wire or other support may be molded as part of the construction of the reservoir after it is formed. The wire or other support may also extend along the top and/or bottom surfaces of the shell.

Another feature that can help maintain the shape of the shell is the inclusion of portions that extend along the top and bottom shell surfaces like ribs or corrugations. Such ribs can extend in any desired direction along these surfaces, and can be of varying lengths, depths, and/or widths. One or more such ribs or corrugations can be used, where the ribs on a single shell may be the same or different from each other. The ribs can also be useful in the molding manufacture of the part. That is, although the shell can be made by dipping or molding, the addition of one or more ribs will particularly be beneficial in a molding process. The ribs or corrugations can help direct fluid flow and maintain patency.

In the preferred embodiment of the invention, length 100 of reservoir 18 is about 3.85 inches (9.78 cm), width 102 is about 2.30 inches (5.84 cm), depth 106 is about 1.00 inches (2.54 cm), and neck diameter 104 is about 0.57 inches (1.45 cm). The angle of transition A is about 44 degrees, the inner radius B of transition area 33 is about 0.235 inches (0.61 cm), the outer radius C of transition area 33 is about 0.229, the neck portion length 107 is about 0.22 inches (0.56 cm), and the transition area length is about 0.22 inches (0.56 cm). In reference to shell thicknesses, thickness 111 of the wall 113 is about 0.40 inches (1.02 cm) while thickness 115 of the neck portion wall 117 is about 0.3 inches (0.76 cm). Reservoir 18 in this preferred embodiment is designed to hold about 85-ml of fluid. However, it is understood that reservoir 18 can be designed to have different dimensions to hold varying capacities of fluid, including capacities of 65-ml and 100-ml, along with other desired volumes. In any case, the depth of a reservoir of the invention, such as depth 106 of reservoir 18, should be small enough that it can be implanted submuscularly in the lower abdomen of the patient and remain virtually undetectable from outside the patient's body. Further, the length 100 and width 102 are selected to fit into the patient lateral to the midline of the lower abdomen.

Referring additionally to FIG. 1, tube 24 is shown as having an adapter 36 between neck portion 34 and tube 24, although tube 24 and adapter 36 are not the only types of devices that can extend from reservoir 18 for fluid communication between reservoir 18 and other adjacent devices or components. For example, additional or different adapters or devices may be connected directly to one end of neck portion 34, in which case any tubing used may optionally be attached to the configuration at some other point distal from shell 26 and neck portion 34. In cases where such a tube is used, however, the tube preferably includes an inner fluid passage extending along its length through which fluid can move to and from shell 26. In one exemplary configuration, tube 24 is a separate component that is sealed to either adapter 36 or neck portion 34 during a molding process as described below. However, tube 24 may be molded as part of the neck portion or otherwise fused or bonded directly to neck portion 34 with an appropriate technique.

Figure 8:
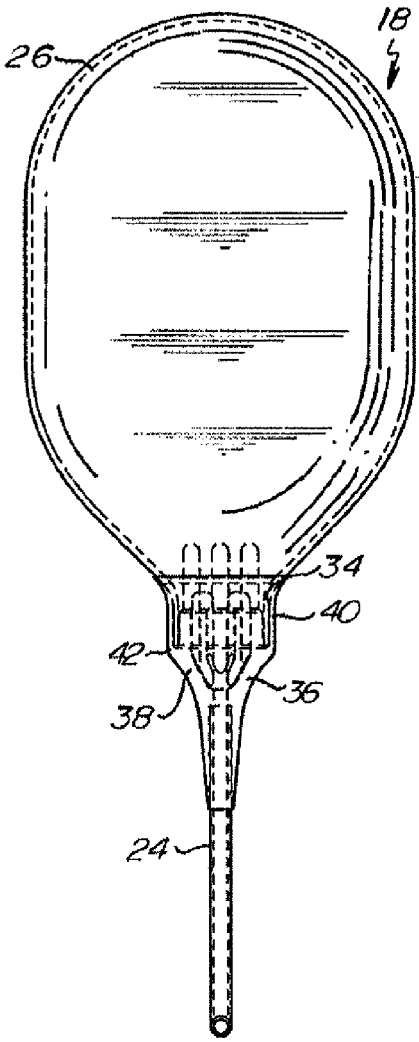
FIG. 8 is a side view of the reservoir of FIG. 2, showing a reservoir shell attached to a support structure or device of an adapter, and a tube attached to the adapter at a sleeve.

Referring to FIG. 8, an exemplary adapter 36 is illustrated with additional detail, which includes a body portion 38 and annular flange 40. Preferably annular flange 40 increases in diameter from the area of tube 24 toward the end of flange 40. Body portion 38 also includes an annular groove 42 that is at the end of flange 40. Body portion 38 also includes an annular groove 42 that is at least partially defined by flange 40 and body portion 38, as illustrated. The width of groove 42 is preferably designed to accept the free edge of shell 26. This is, neck portion 34 is designed to fit into annular groove 42. Flange 40 is preferably flexible enough that it can conform generally to the outside shape of shell 26 in both its expanded and collapsed conditions. Further, when neck portion 34 is positioned within groove 42, the inside surface of flange 40 may be adhered or otherwise bonded to the outside surface of shell 26 at or adjacent to neck portion 34. In addition, or alternatively, an outside surface of body portion 38 may be bonded to an inside surface of annular neck portion 34 in order to secure shell 26 to adapter 34. In addition, the inside surface of flange 40 may also be adhered to a portion of shell 26 beyond neck portion 34, such as where the diameter of shell 26 increases and beyond the area where neck portion 34 is positioned within annular flange 40. It is contemplated that the thickness of the neck portion may vary and/or the width of the annular gap may change along its length. For any portions of the reservoir components that are bonded to each other, any medical grade adhesive, insert molded bonding technology or method, or the like may be used.

When a penile prosthesis device utilizing a reservoir of the invention is implanted in a user, shell 26 may be repeatedly deflated and inflated. During deflation, the shell 26 can collapse inwardly on itself at least slightly, which may also cause it to flex at neck portion 34 (as well as other parts of shell 26). Such repeated flexing could cause fatigue at neck portion 34, which could cause a gradual thinning of the wall and eventual failure (e.g., leakage) between shell 26 and flange 40. Thus, flange 40 is desirably configured to provide additional support at neck portion 34 while also providing a smooth transition from body portion 38 of adapter 36 to shell 26 and minimizing areas of stress concentration. Adapter 36 may also include a wide variety of other features, such as the support structures or elements designed to minimize or prevent fluid flow blockage caused by the collapse of an attached reservoir, such as the type described in U.S. patent application Ser. No. 10/957,190, entitled "Fluid Reservoirs for Penile Implant Devices and Method of Manufacturing", which is also commonly owned by the assignee of the present invention, the entire contents of which are hereby incorporated by reference.

In another aspect of the invention, a lubricity enhancing coating such as a parylene coating or the like may be applied to at least a portion of an inside surface of a reservoir, in U.S. Pat. No. 6,558,315 (Kuyava) and U.S. Patent Application Publication No. 2003/0220540 (Kuyava), both of which are commonly owned by the assignee of the present invention Another example of the use of parylene coatings for artificial sphincters is further described, for example, in U.S. Patent Application Publication No. 2003/0028076 (Kuyava et al), which is also commonly owned by the assignee of the present invention. A parylene coating may be applied by using conventionally known techniques such as vapor deposition or the like, for example. Such a lubricity enhancing coating can improve the frictional characteristics of an inside surface of a reservoir and the durability of the reservoir. This can improve reliability of a reservoir by controlling the frictional effects on an inside surface of a reservoir that can result during inflation and deflation of such reservoirs.

In another aspect of the invention, at least some of the components of the penile implant devices can be treated on their outer surfaces with an antimicrobial agent, including the cylinders, pump and/or reservoir. Examples of treating antimicrobial agents on implantable medical devices are described, for example, in U.S. Pat. No. 6,534,112 (Bouchier et al) and U.S. Patent Application Publication No. 2004/0040500 (Bouchier et al.) both of which are commonly owned by the assignee of the present invention.

When the reservoir 18 and optional adapter 36 are constructed of a single piece, the configuration may be formed by injection molding, which can use liquid silicone rubber, for example, or by compression molding, which may use gum rubber or high compression rubber, such as silicone, for example. Methods of injection molding may include the use of a flowable material (e.g., thermoplastic or thermosetting), such as a polymeric material, and a mold. The flowable material is placed at a desired temperature (e.g., by heating) and is injected into a cavity to produce a molded component (here, a fluid reservoir). The mold is then opened, optionally after cooling, and the molded component can be removed from the mold and optionally cured. In particularly preferred embodiments, a reservoir can be prepared by injection molding methods. The reservoir may be molded to become attached to a tube at the exit orifice of the reservoir shell. This is, by preferred injection molding processes, an elongated tube, such as tube 24, can be attached to the reservoir during a process of injection molding the reservoir. To do this, the tube can be positioned onto a mandrel of a mold. A relatively spherical, solid mold core pin is also included, which a form of the inside of the reservoir. Outer sections of the mold that define the outer surfaces of the reservoir are then placed around the core pin to thereby create a cavity that is the size and shape of the fluid reservoir. The entire mold is then brought to a processing temperature, and then a predetermined amount of a desired material is injected into the mold over the tube and the spherical mode core pin to fill the cavity. After a predetermined time, the mold is opened and the reservoir with the attached tube is removed from the mold, with the sleeve thereby becoming molded around the outside diameter of the tube as the sleeve body portions of the reservoir are formed.

The reservoir, being of a flexible material ca be removed from around the core pin following cooling or curing of the flexible material as necessary. Removal of the reservoir from the core pin can be done by stretching the reservoir material around the core pin. Optionally, water, soap, air, or a combination of these, can be used to separate the inside surface of the reservoir from the core pin. One especially convenient and effective way to introduce any materials such as water, soap and air, to the space between the core pin and the inside of the reservoir, is to inject any one or more of these through the tube connected to the reservoir. In this method, there is an air poppet included in the shell mold that introduces a burst of air into the shell end opposite of the neck. A plastic fixture or removal tool is placed over the mandrel, which is slightly larger than the shape of the shell, after the silicone has been molded over the mandrel that 'grabs' the air-inflated shell. In this way, the fixture with the inflated shell is pulled off the mandrel.

As one example, a reservoir may be made from liquid silicone rubber, such as a high consistency gum rubber silicone. A mold temperature in the range of 250 deg. F. (121 deg. C.) to 275 deg. F. (135 deg. C.) may be used. Also, a molding time of approximately 2.5 minutes may be used. Alternatively, the reservoir may be made from any other useful, flexible medical or industrial material that is biologically inert and non-reactive with the inflating fluid that will be contained by the reservoir. The material may be a thermoset or thermoplastic. Specific examples of useful materials can include thermosetting silicone rubber (e.g., polydimethyl siloxane), thermosetting or thermoplastic urethanes, C-flex, santoprene thermoplastics, and the like.

Figure 15:
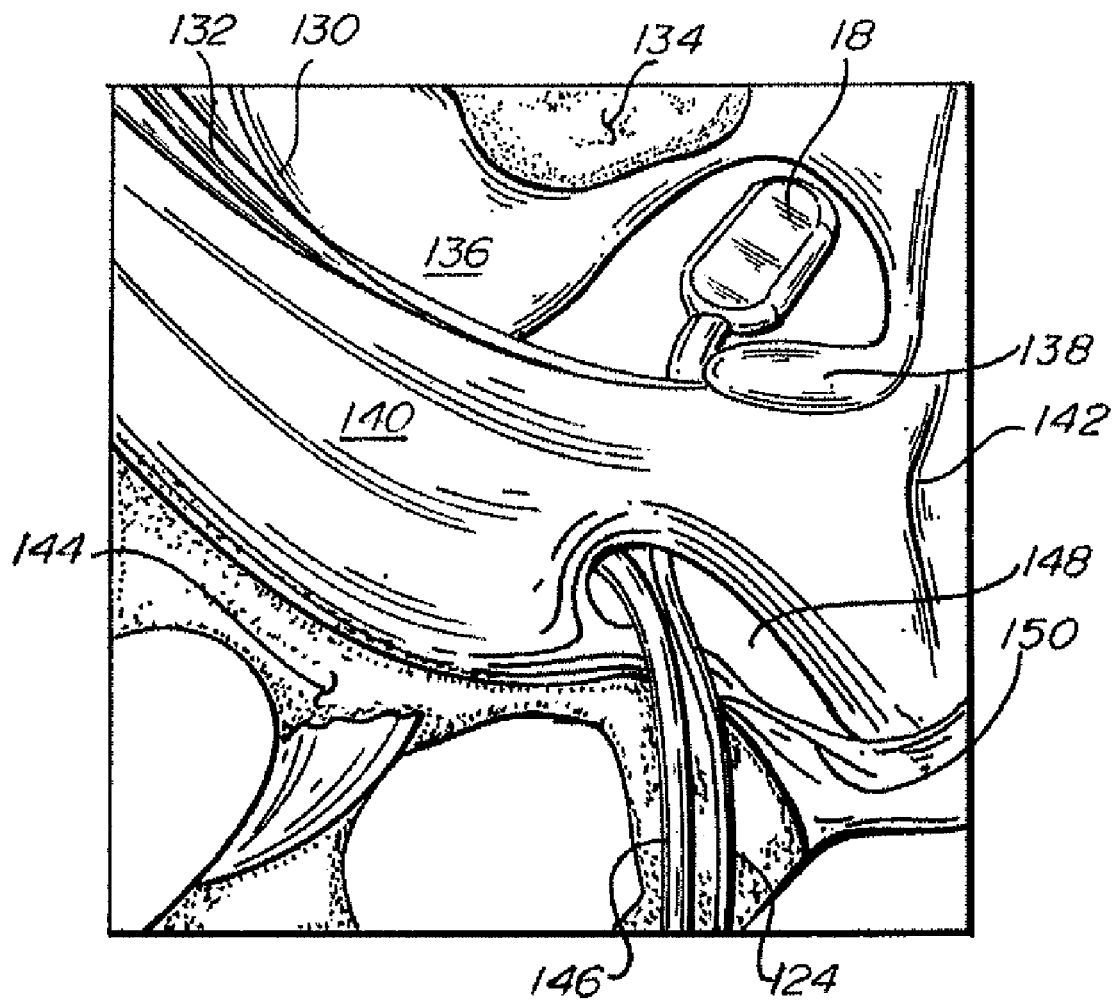
FIG. 15 depicts the reservoir implanted in a patient in a location that is posterior to the puborectalis muscle and anterior to the abdominal fascia.

FIG. 15 depicts an example of the reservoir 18 implanted within a patient, tube 24 is also depicted. The pertinent anatomy is identified as follows: (1) transverse abdominis muscle 130; (2) internal oblique muscle 132; (3) orthotopic bladder 134; (4) transversalis fascia or abdominal fascia 136; (5) rectus abdominis muscle or puborectalis muscle 138; (6) external oblique muscle 130; (7) linea alba 142; (8) pubic ramus 144; (9) spermatic cord 146; (10) external inguinal ring 148; (11) pubic tubercle 150; and (12) symphysis pubis 152.

Figure 9:
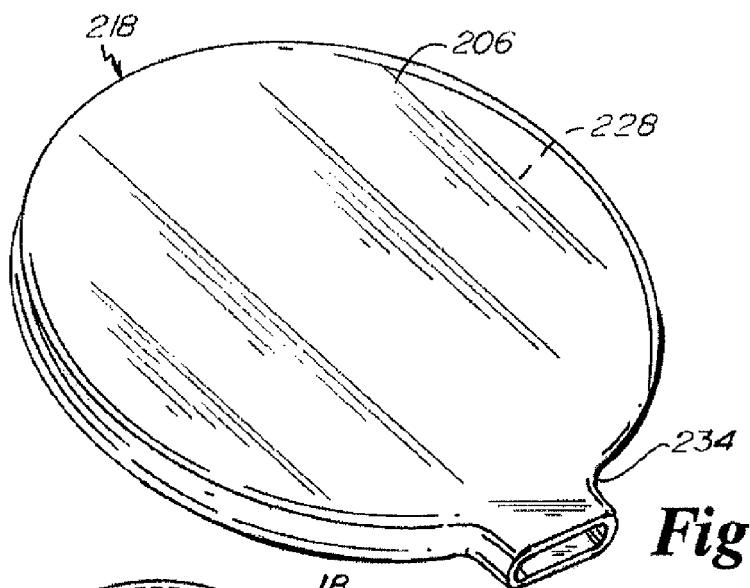
FIG. 9 is a perspective view of one embodiment of a reservoir of the invention.
Figure 11:
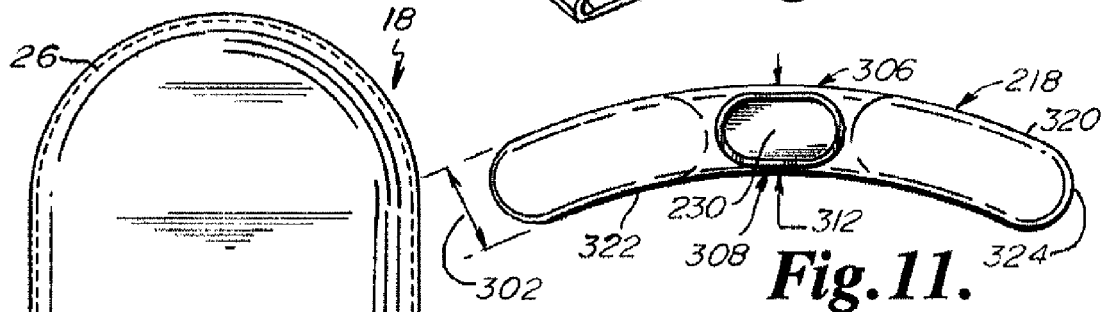
FIG. 11 is a side view of the reservoir of FIG. 9 as viewed from the neck opening side of the reservoir.
Figure 10:
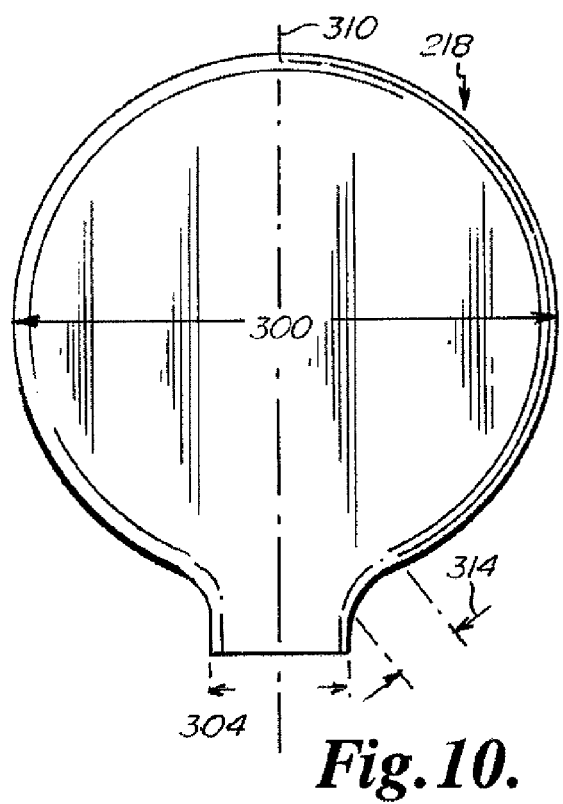
FIG. 10 is a top view of the reservoir of FIG. 9.

FIGS. 9 through 11 further illustrate one exemplary embodiment of reservoir 218 of the present invention, which generally includes a shell 226 having an interior space 228 and an opening 230 at one end. A neck portion 234 extends from shell 226 at opening 230 for connection with a tube, such as tube 224 of prosthesis device 210. Neck portion 234 may be directly connected to tube 224 or another component, or an adapter or other device can be used between neck portion 234 and tube 224 to provide a smooth transition between these two components. Such an adapter may be particularly useful, for example, when the neck portion has a different cross-sectional shape (e.g., elliptical) than the cross-sectional shape (e.g., circular) of the tube to which the neck portion is attached. Any additional devices or adapters that are provided between tube 224 and neck portion 234 may be directly molded to one or both components, or may be adhered or otherwise attached to one or both components to prevent fluid leakage and allow for smooth fluid flow. In any case, the transitions between tube 224 and neck portion 234 should not inhibit the flow of fluid to and from interior space 228 of reservoir 218.

Reservoir 218 is generally provided in a relatively flat, circular shape as illustrated, which includes shell 226 that is shaped as a relatively flat disc. Reservoir 218 is preferably symmetrical or generally symmetrical about its centerline 310, with shell 226 having a diameter 300 and a depth or thickness 302. Neck portion 234 extends from shell 226 at one end, and is generally oval or elliptical in shape. Neck portion 234 has a width 304 and a depth 312 that is equal to or at least slightly smaller than depth or thickness 302 of shell 226. In addition, neck portion 234 has a material thickness 306. The material from which the remainder of reservoir 218 is made may be the same or a different thickness than material thickness 306. A small curved portion 314 that curves in the opposite direction of the outer periphery of shell 226 can be provided in the transition area between shell 226 and neck portion 234.

Shell 226 also includes a slight curvature relative to the neck portion 234 or as compared to a planar device, which is most visible in FIG. 11. This curvature has a radius 308 when viewed from the bottom or neck area 234 of shell 226. The center of a circle that defines the radius 308 would include an axis that extends in the same direction as centerline 310. Although neck portion 234 is not shown as following the same curvature as shell 226, it is understood that neck portion 234 may also have a radius that is similar to radius 308 (i.e., neck portion 234 may follow the same curvature as shell 226), or neck portion 234 may alternatively have a radius that is smaller or larger than radius 308.

Referring particularly to FIG. 11, shell 226 includes a top surface 320 and an opposite bottom surface 322 that is spaced from top surface 320 by a distance equal to depth 302. A curved edge surface 324 extends between top surface 320 and bottom surface 322 along most of the peripheral edge of shell 226, except in the area of opening 230. Top surface 320 is preferably a slightly curved surface that is generally parallel to bottom surface 322, which is a surface that has a similar curve. However, it is possible that these surfaces 320, 322 are angled relative to each other such that depth 302 varies within the interior portion of shell 226. The curved edge surface 324 between top surface 320 and bottom surface 322 can be provided with a material thickness that is greater than the material thickness of either or both of top and bottom surfaces 320, 322. Alternatively, the material thickness of curved edge surface 324 can be less than or the same as the material thickness of top and bottom surfaces 320, 322. In any case, curved edge surface 324 is shaped and sized to promote the integrity of the shape of shell 226. This feature is particularly advantageous to maintain the shape of reservoir 218 when the reservoir is subjected to external pressures cause by the patient's internal organs and bodily fluids after it is implanted in the body.

In one particular exemplary embodiment, diameter 300 of shell 226 is about 3.30 inches (8.38 cm), thickness 102 is about 0.50 inches (1.27 cm) and width 304 of neck portion 234 is about 0.75 inches (1.91 cm). Further, the thickness of top and bottom surfaces 320, 322 is about 0.025 inches (0.064 cm) and thickness 306 of neck portion 234 is about 0.025 inches (0.064 cm). The internal volume of reservoir 218 in this embodiment is about 3.63 in$^3$ (59.49 cm$^3$). However, it is understood that reservoir 218 can be designed to have different wall thickness and overall dimensions to hold varying capacities of fluid, including capacities of 65-ml and 100-ml, along with other desired volumes. In any case, the depth of a reservoir of the invention, such as depth 302 of reservoir 218, should be small enough that the reservoir can be implanted submuscularly in the lower abdomen of the patient and remain virtually undetectable from outside the patient's body. The diameter 300 is also selected to fit into the patient lateral to the midline of the lower abdomen. Further, the curvature of shell 226 of this exemplary embodiment has a radius 308 of about 6 inches (15.24 cm); however, radius 308 can be chosen to be any appropriate size that allows placement of shell 226 submuscularly in the lower abdomen.

Figure 12:
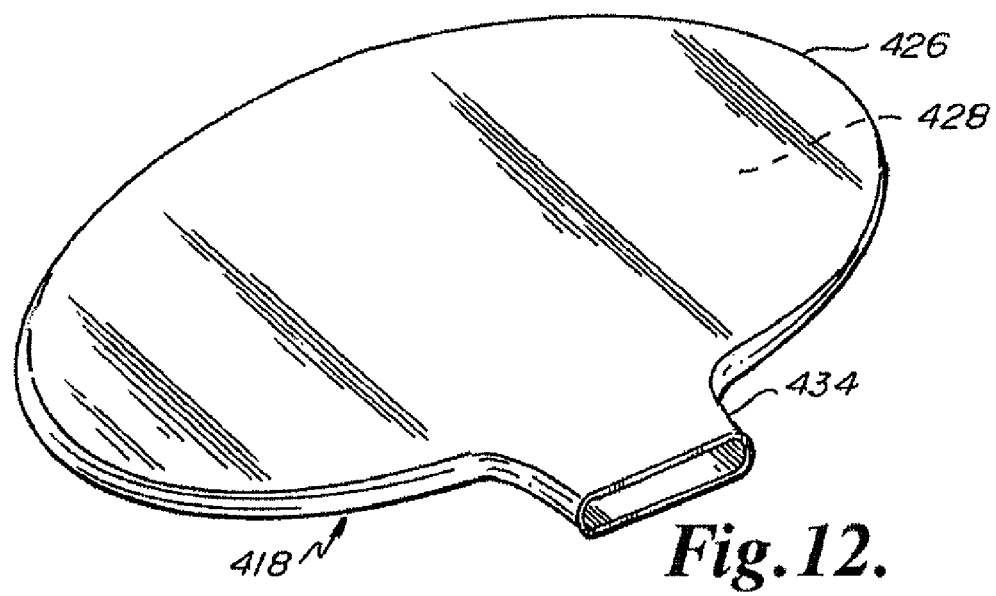
FIG. 12 is perspective view of another embodiment of a reservoir of the invention.
Figure 13:
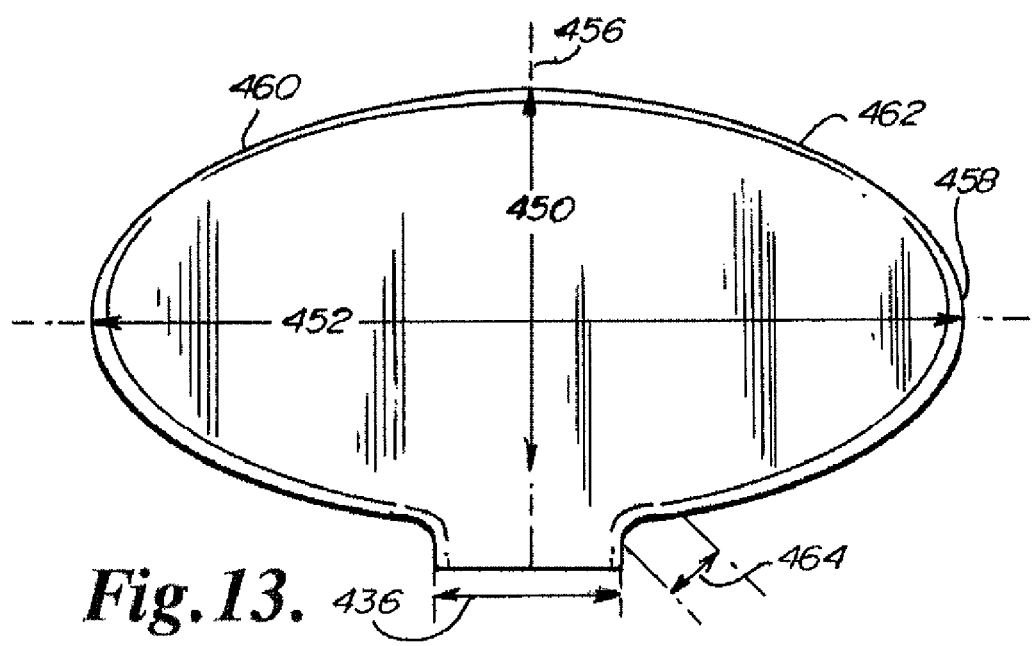
FIG. 13 is a top view of the reservoir of FIG. 12.
Figure 14:
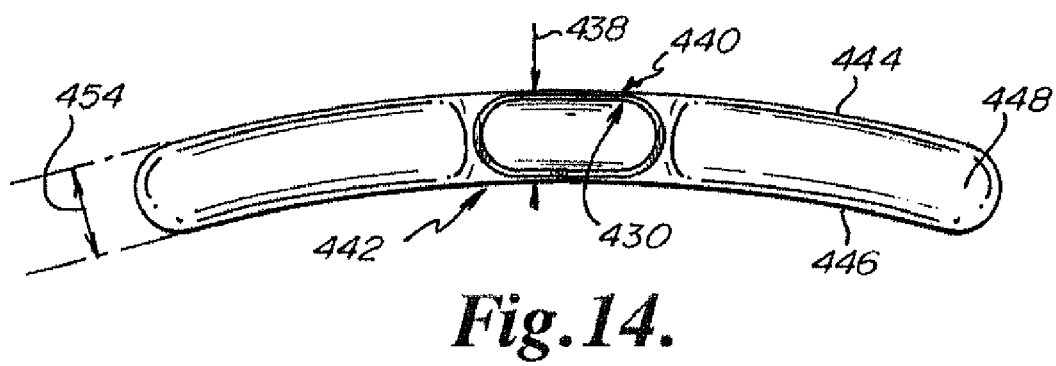
FIG. 14 is a side view of the reservoir of FIG. 12 as viewed from the neck opening side of the reservoir.

FIGS. 12 through 14 further illustrate another exemplary embodiment of reservoir 418 of the present invention, which generally includes a shell 426 having an interior space 428 and an opening 430 at one end. A neck portion 434 extends from shell 426 at opening 430 for connection with a tube, such as tube 24 of prosthesis device 10. Neck portion 434 may be directly connected to tube 24 or another component in a prosthesis device, or an adapter or other device can be used between neck portion 434 and tube 24 to provide a smooth transition between these two components. Such an adapter may be particularly useful, for example, when the neck portion has a different cross-sectional shape (e.g., elliptical) than the cross-sectional shape (e.g., circular) of the tube to which the neck portion is attached. Any additional devices or adapters that are provided between tube 24 and neck portion 434 may be directly molded to one or both components, or may be adhered or otherwise attached to one or both components to prevent fluid leakage and allow for smooth fluid flow. In any case, the transitions between tube 24 and neck portion 434 should not inhibit the flow of fluid to and from interior space 428 of reservoir 418.

Reservoir 418 is generally provided in a relatively flat, oval-like shape as illustrated, which includes shell 426 having a height 450, a width 452, and a depth or thickness 454. Height 450 is shorter than width 452, thereby creating the non-circular or oval-like shape of shell 426. Reservoir 418 is preferably symmetrical or generally symmetrical about a centerline 456 that extends from the shell throughout the center of neck portion 434, as shown in FIG. 13. Shell 426 (not including neck portion 434) is preferably symmetrical or generally symmetrical about a centerline 458 that is perpendicular to centerline 456. Neck portion 434 extends from shell 426 at one end, and is generally oval or elliptical in shape. The outer periphery of reservoir 418 includes shell 426 having two curved edge portions 460 and 462, where edge portion 460 extends from centerline 456 at the top of shell 426 around the left side of shell 426 to neck portion 434, and edge portion 462 extends from centerline 456 at the top of shell 426 around the right side of shell 426 to neck portion 434. Curved edge portions 460, 462 provide the outside boundary for a portion of shell 426 that decreases in height 450 when moving away from centerline 456, and which also decreases in width 452 when moving away from centerline 458. A small curved portion 464 that curves in the opposite direction of the outer periphery of shell 426 can be provided in the transition area between shell 426 and neck portion 434.

Neck portion 434 has a width 436 and a depth 438 that is equal to or at least slightly smaller than depth or thickness 454 of shell 426. In addition, neck portion 434 has a material thickness 440. The material from which the remainder of reservoir 418 is made may be the same or a different thickness than material thickness 440.

Shell 426 also includes a slight curvature relative to the neck portion 434 or as compared to a planar device, which is most visible in FIG. 14. This curvature has a radius 442 when viewed from the bottom or neck area 434 of shell 426. Although neck portion 434 is not shown as following the same curvature as shell 426, it is understood that neck portion 434 may also have a radius that is similar to radius 442 (i.e., neck portion 434 may follow the same curvature as shell 426), or neck portion 434 may alternatively have a radius that is smaller or larger than radius 442.

Referring particularly to FIG. 14, shell 426 includes a top surface 444 and an opposite bottom surface 446 that is spaced from top surface 444 by a distance equal to depth 454. A curved edge surface 448 extends between top surface 444 and bottom surface 446 along most of the peripheral edge of shell 426, except in the area of opening 430. Top surface 444 is preferably a slightly curved surface that is generally parallel to bottom surface 446, which is a surface that has a similar curve, although it is possible that these surfaces 444, 446 are angled relative to each other such that depth 454 varies within the interior portion of shell 426. It is also possible that surfaces 444, 446 have different curvatures relative to each other or that one of the surfaces is generally straight. Surfaces 444, 446 may also curve in opposite directions from each other.

The curved edge surface 448 between top surface 444 and bottom surface 446 can be provided with a material thickness that is greater than the material thickness of either or both of top and bottom surfaces 444, 446. Alternatively, the material thickness of curved edge surface 448 can be less than or the same as the material thickness of top and bottom surfaces 444, 446. In any case, curved edge surface 248 is shaped and sized to promote the integrity of the shape of shell 426. This feature is particularly advantageous to maintain the shape of reservoir 418 when the reservoir is subjected to external pressures cause by the patient's internal organs and bodily fluids after it is implanted in the body. In yet another alternative, the edge surface 448 could be more square or angular in shape, where it is contemplated that the outside surface of edge surface 448 can be more squared than the portion of surface opposite edge surface that faces the inside of the shell, which may be curved, for example.

In one particular exemplary embodiment of reservoir 418, width 452 of shell 426 is about 4.50 inches (11.43 cm), height 450 is about 2.50 inches (6.35 cm), depth 454 is about 0.50 inches (1.27 cm), and width 436 of neck portion 434 is about 1.00 inches (2.54 cm). Further, the thickness of top and bottom surfaces 444, 446 is about 0.025 inches (0.064 cm) and thickness 440 of neck portion 434 is about 0.025 inches (0.064 cm). The internal volume of reservoir 418 in this embodiment is about 3.80 in$^3$ (62.27 cm$^3$). However, it is understood that reservoir 418 can be designed to have different dimensions to hold varying capacities of fluid, including capacities of 65-ml and 100-ml, along with other desired volumes. In any case, the depth of a reservoir of the invention, such as depth 454 of reservoir 418, should be small enough that the reservoir can be implanted submuscularly in the lower abdomen of the patient and remain virtually undetectable from outside the patient's body. Further, the curvature of shell 426 of this exemplary embodiment has a radius 442 of about 6 inches (15.24 cm); however, radius 442 can be chosen to be any appropriate size that allows placement of shell 426 submuscularly in the lower abdomen.

Figure 16:
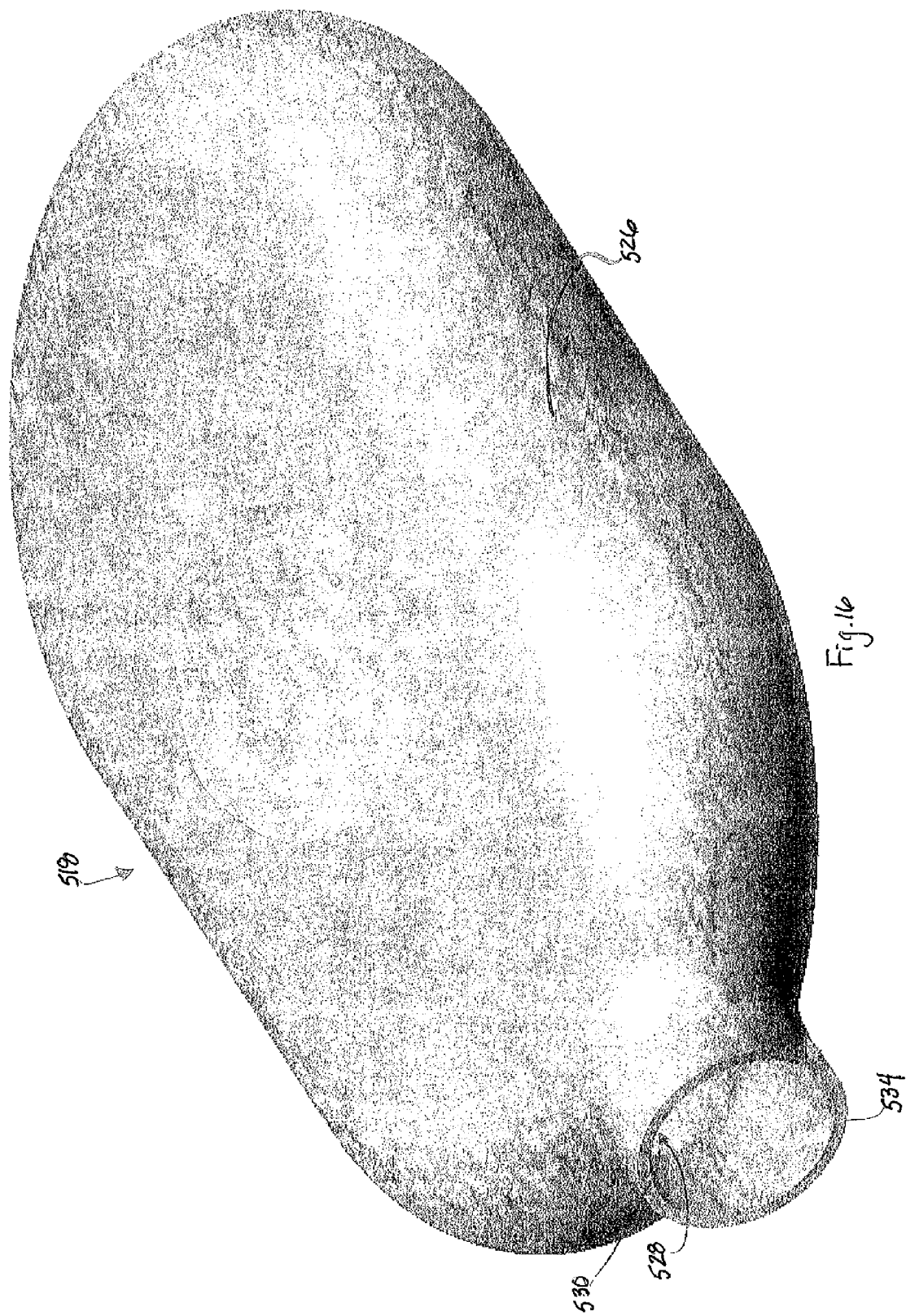
FIG. 16 is a perspective view of an embodiment of a reservoir of the invention.
Figure 17:
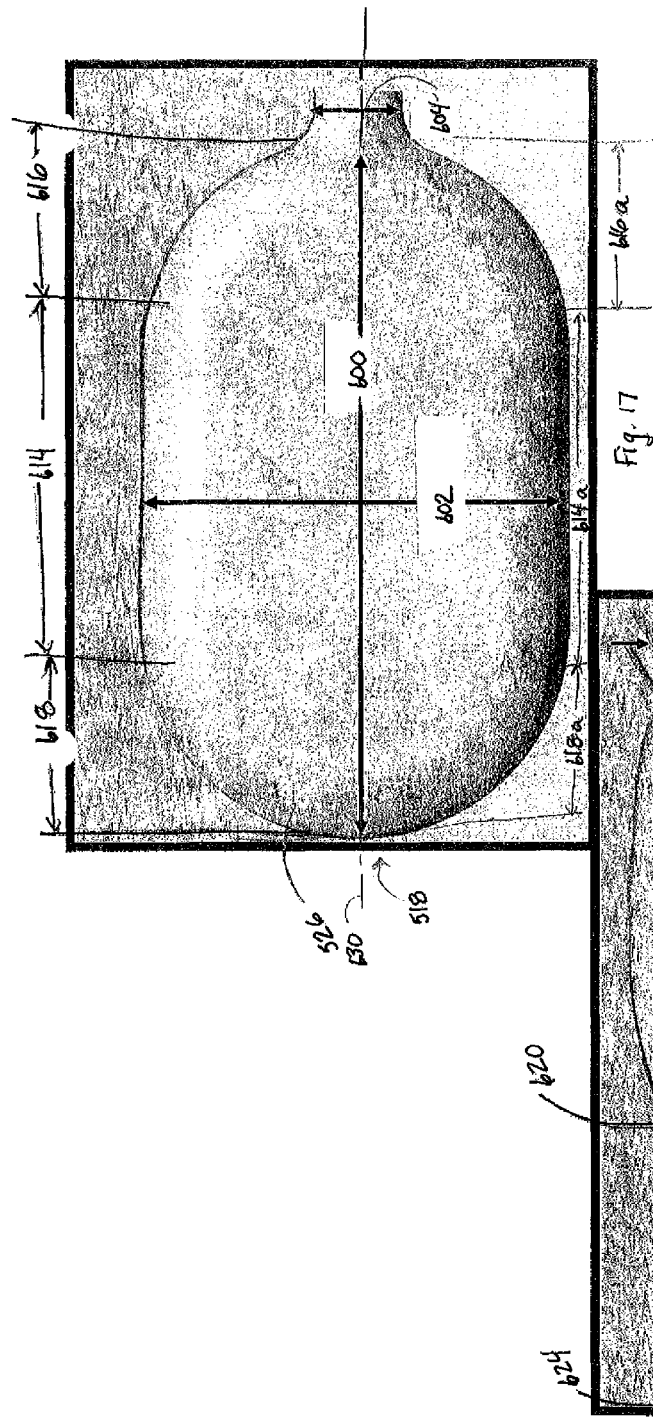
FIG. 17 is a top view of the reservoir of FIG. 16.
Figure 18:
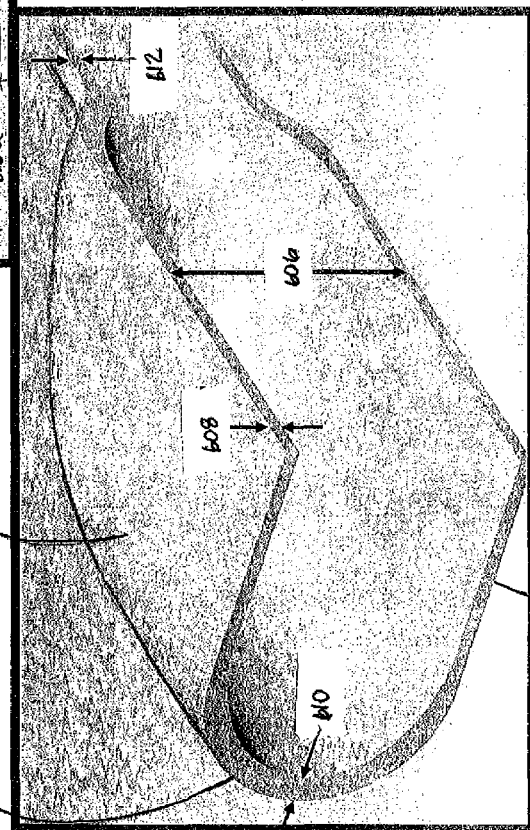
FIG. 18 is a partially cut-away perspective view of the reservoir of FIG. 16.

FIGS. 16 through 18 further illustrate one exemplary embodiment of reservoir 518 of the present invention, which generally includes a shell 526 having an interior space 528 and an opening 530 at one end. A neck portion 534 extends from shell 526 at opening 530 for connection with a tube, such as tube 24 of prosthesis device 10. Neck portion 534 may be directly connected to tube 24 or another component, or an adapter or other device can be used between neck portion 534 and tube 24 to provide a smooth transition between these two components. Any additional devices or adapters that are provided between tube 24 and neck portion 534 may be directly molded to one or both components, or may be adhered or otherwise attached to one or both components to prevent fluid leakage and allow for smooth fluid flow. In any case, the transitions between tube 24 and neck portion 534 should not inhibit the flow of fluid to and from interior space 528 of reservoir 518.

Referring particularly to FIGS. 17 and 18, reservoir 518 is generally provided in an exemplary flat, elongated shape as illustrated, which includes shell 526 having a length 600, a width 602, and a depth or thickness 606. Reservoir 518 is preferably symmetrical or generally symmetrical about its centerline 630, shown in FIG. 17. Width 602 is preferably relatively constant along at least a portion of length 600, and is more preferably relatively constant along at least half of the length 600 of shell 526, although it is possible that the width 602 is constant along less than half of the length 600 of shell 526. A straight portion 614 of one edge of shell 526 is located between curved portions 616 and 618. Curved portion 616, which is shown on the top edge of shell 526 in FIG. 17, has a corresponding (i.e., mirror image) curved portion 616a on the opposite or bottom edge of shell 526. Curved portions 616 and 616a provide the outside boundary for a portion of shell 526 that decreases in width from width 602 at straight portions 614 and 614a down toward a diameter 604 of neck portion 534. A small curved portion that curves in the opposite direction of portion 616 can be provided in the transition area between portion 616 and neck portion 534. Curved portion 618, which is shown on the top edge of shell 526 in FIG. 17, is a curved edge that extends from straight portion 614 on one edge of shell 526, to the centerline 630 of shell 526. Curved portion 618a continues from curved portion 618 around the bottom edge of shell 526 and around to the straight portion 614a of shell 526. In this exemplary embodiment, length 600 has a greater length than width 602, and both length 600 and width 602 are greater in length than thickness or depth 606.

Referring particularly to FIG. 18, a section of shell 526 is illustrated in cross-section to better view the various thicknesses of the shell portions. Shell 526 includes a top surface 620 and an opposite bottom surface 622 that is spaced from top surface 620 by a distance equal to depth 606. A curved edge surface 624 extends between top surface 620 and bottom surface 622 along most of the peripheral edge of shell 526, except in the area of opening 630. Top surface 620 is preferably a planar surface that is generally parallel to bottom surface 622, although it is possible that these surfaces 620, 622 are angled relative to each other such that depth 606 varies within the interior portion of shell 526. Top surface 620 and bottom surface 622 have a thickness 608, neck portion 534 has a thickness 612, and curved edge surface 624 has a thickness 610. Thickness 608 is preferably generally the same as or slightly greater than thickness 612. Thickness 610 is preferably greater than thicknesses 608 and 612 to promote the integrity of the shape of shell 526. Alternatively, thickness 610 can be less than or the same as thicknesses 608 and 612. This feature is particularly advantageous to maintain the shape of reservoir 518 when the reservoir is subjected to external pressures cause by the patient's internal organs and bodily fluids after it is implanted in the body. More preferably, thickness 610 is about twice as large as thicknesses 608 and 612. The increase in thickness from either of the top and bottom surfaces 620, 622 to curved edge surface 624 is preferably a gradual increase in the form of a tapered change in thickness between the various surfaces of reservoir 518.

An additional way to maintain the integrity of the shell shape is to provide an internal or external support material that is attached to or otherwise situated relative to the shell. For one example, a wire, such as may be constructed of nitinol, may be shaped to generally match the outer shape of the reservoir. The wire or other support may be molded as part of the construction of the reservoir, or may alternatively be inserted or otherwise attached to the reservoir after it is formed. The wire or other support may also extend along the top and/or bottom surfaces of the shell.

Another configuration that can help maintain the shape of the shell is the inclusion of portions that extend along the top and bottom shell surfaces like ribs or corrugations. Such ribs can extend in any desired direction along these surfaces, and can be of varying lengths, depths, and/or widths. One or more such ribs or corrugations can be used, where the ribs on a single shell may be the same or different from each other. The ribs can also be useful in the molding manufacture of the part. That is, although the shell can be made by either dipping or molding, the addition of one or more ribs will particularly be beneficial in a molding process. The ribs or corrugations can help direct fluid flow and maintain patency.

In one particular exemplary embodiment, length 600 of reservoir 518 is about 3.75 inches (9.53 cm), width 602 is about 2.25 inches (5.72 cm), depth 606 is about 0.75 inches (1.91 cm), and neck diameter 604 is about 0.50 inches (1.27 cm). Further, thickness 610 of curved portion 624 is about 0.080 inches (0.203 cm), thickness 608 of top and bottom surfaces 620 and 622 is about 0.040 inches (0.102 cm) and thickness 612 of neck 534 is about 0.040 inches (0.102 cm). The internal volume of reservoir 518 in this embodiment is about 3.92 in$^3$ (64.24 cm$^3$). However, it is understood that reservoir 518 can be designed to have different dimensions to hold varying capacities of fluid, including capacities of 65-ml and 100-ml, along with other desired volumes. In any case, the depth of a reservoir of the invention, such as depth 606 of reservoir 518, should be small enough that it can be implanted submuscularly in the lower abdomen of the patient and remain virtually undetectable from outside the patient's body. Further, the length 600 and width 602 are selected to fit into the patient lateral to the midline of the lower abdomen.

The present invention has now been described with reference to several embodiments thereof. The entire disclosure of any patent or patent application identified herein is hereby incorporated by reference. The foregoing detailed description and examples have been give for clarity of understanding only. No unnecessary limitations are to be understood therefrom. It will be apparent to those skilled in the art that many changes can be made in the embodiments described without departing from the spirit or scope of the invention. Thus, the scope of the present invention should be limited to the structures described herein, but only by those structures.

What is claimed:

1. A method of implanting a medical device, comprising the steps of:
    implanting an implantable element within the pelvic region of a patient, wherein said implantable element is capable of inflation and deflation via fluid transfer to and from the element;
    coupling said implantable element to a fluid reservoir enabling fluid to be drawn from said fluid reservoir for said inflation and returned to said fluid reservoir for said deflation, wherein said fluid reservoir is approximately one inch or less in depth; and
    implanting said fluid reservoir into the patient in a location that is in front of the puborectalis muscle and behind the transversalis fascia.

2. The method of claim 1, wherein said implantable element comprises a penile prosthesis.

3. A fluid reservoir for use in a penile prosthesis device, the reservoir comprising:
    a shell having a top surface, a bottom surface spaced from the top surface by a distance equal to the height of a curved edge portion that extends from the top and bottom surfaces, an inner fluid storage area, and a centerline extending from one edge of the shell to an opposite edge of the shell, wherein the top and bottom surfaces generally curve about an axis that is parallel to the centerline of the shell; and
    a neck portion extending from the curved edge portion of the shell, wherein the centerline of the shell also extends through a center point of the neck portion.

4. The fluid reservoir of claim 3, wherein the top surface is generally parallel to the bottom surface and wherein the top surface is approximately one inch or less in distance from said bottom surface.

5. The fluid reservoir of claim 3, further comprising an adapter extending from the neck opening of the shell.

6. The fluid reservoir of claim 5, wherein the adapter and the shell are integrally molded as a single piece.

7. The fluid reservoir of claim 6, wherein the shell is compression molded.

8. The fluid reservoir of claim 6, wherein the shell is expandable to an expanded state and collapsible to a collapsed state in response to fluid movement into and out of the inner fluid storage area, respectively.

9. The fluid reservoir of claim 5, wherein the adapter and the shell are injection molded.

10. The fluid reservoir of claim 5, wherein the adapter and the shell are compression molded.

11. The fluid reservoir of claim 5, wherein the adapter is bonded to the shell.

12. The fluid reservoir of claim 5, wherein the shell is injected molded.

13. A method of implanting a penile prosthesis device, comprising the steps of:
   providing a prosthesis device comprising:
      a fluid reservoir comprising a shell having a top surface, a bottom surface spaced from the top surface by a distance equal to the height of a curved edge portion that extends from the top and bottom surfaces, and a centerline extending from one edge of the shell to an opposite edge of the shell, wherein the top and bottom surfaces are curved, and a neck portion extending from the curved edge portion of the shell, wherein the centerline of the shell also extends through a center point of the neck portion;
      a pump fluidly connected to the reservoir; and
      a pair of inflatable penile prostheses fluidly connected to the reservoir;
   implanting the pump into the scrotum of a patient;
   implanting the pair of inflatable penile prostheses into the corpus cavernosae of the patient; and
   implanting the reservoir into the patient in a location that is in front of the puborectalis muscle and behind the abdominal fascia.

14. A fluid reservoir for use in a penile prosthesis device, the reservoir comprising:
   a shell having a top surface, a bottom surface spaced from the top surface by a distance equal to the height of a curved edge portion that extends from the top and bottom surfaces, a first edge having a straight portion and two curved portions, and a second edge spaced from the first edge, the second edge having two curved portions and a straight portion that is parallel to the straight portion of the first edge; and
   a neck portion extending from the curved edge portion of the shell;
   wherein the top surface and bottom surfaces each have a thickness that is smaller than a thickness of the curved edge portion.

15. The fluid reservoir of claim 14, wherein the top and bottom surfaces each comprise a planar portion, and wherein the planar portions of the top and bottom surfaces are generally parallel.

16. The fluid reservoir of claim 15, wherein the top surface is approximately one inch or less in distance from said bottom surface.

17. The fluid reservoir of claim 14, further comprising an adapter extending from the neck opening of the shell.

18. The fluid reservoir of claim 17, wherein the adapter and the shell are integrally molded as a single piece.

19. The fluid reservoir of claim 17, wherein the adapter and the shell are injection molded.

20. The fluid reservoir of claim 17, wherein the adapter and the shell are compression molded.

21. The fluid reservoir of claim 17, wherein the adapter is bonded to the shell.

22. The fluid reservoir of claim 14, wherein the shell is injected molded.

23. The fluid reservoir of claim 14, wherein the shell is compression molded.

24. The fluid reservoir of claim 14, wherein the shell is expandable to an expanded state and collapsible to a collapsed state in response to fluid movement into and out of the inner fluid storage area, respectively.

25. A method of implanting a penile prosthesis device, comprising the steps of:
   providing a prosthesis device comprising:
      a fluid reservoir comprising a shell having a top surface and a bottom surface spaced from each other by a distance equal to the height of a curved edge portion that extends from the top and bottom surfaces, and a neck portion extending from the curved edge portion of the shell, wherein the top surface and bottom surface each have a thickness that is smaller than a thickness of the curved edge portion;
      a pump fluidly connected to the reservoir; and
      a pair of inflatable penile prostheses fluidly connected to the reservoir;
   implanting the pump into the scrotum of a patient;
   implanting the pair of inflatable penile prostheses into the corpus cavernosae of the patient; and
   implanting the reservoir into the patient in a location that is in front of the puborectalis muscle and behind the abdominal fascia.

* * * * *